US008975017B2

(12) United States Patent
Gumbrecht et al.

(10) Patent No.: US 8,975,017 B2
(45) Date of Patent: Mar. 10, 2015

(54) PROCESS FOR CONCENTRATING NUCLEIC ACID MOLECULES (75) Inventors: Walter Gumbrecht, Herzogenaurach (DE); Peter Paulicka, Erlangen (DE); Manfred Stanzel, Erlangen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 477 days.

(21) Appl. No.: 12/734,934

(22) PCT Filed: Nov. 3, 2008

(86) PCT No.: PCT/EP2008/064876
§ 371 (c)(1),
(2), (4) Date: Jun. 3, 2010

(87) PCT Pub. No.: WO2009/071404
PCT Pub. Date: Jun. 11, 2009

(65) Prior Publication Data
US 2010/0248242 A1    Sep. 30, 2010

(30) Foreign Application Priority Data
Dec. 3, 2007  (EP) .................................... 07023377

(51) Int. Cl.
*C12Q 1/68* (2006.01)
*G01N 33/48* (2006.01)

(52) U.S. Cl.
CPC ............ *C12Q 1/6806* (2013.01); *C12Q 1/6825* (2013.01); *C12Q 1/6834* (2013.01); *C12Q 1/6837* (2013.01)
USPC ................................................ 435/6; 436/94

(58) Field of Classification Search
CPC ............................ C12Q 1/6825; C12Q 1/6834
See application file for complete search history.

(56) References Cited

U.S. PATENT DOCUMENTS

| 4,654,267 | A | | 3/1987 | Ugelstad et al. | |
|---|---|---|---|---|---|
| 5,445,971 | A | * | 8/1995 | Rohr .............................. | 436/526 |
| 6,204,033 | B1 | | 3/2001 | Müller-Schulte | |
| 6,280,952 | B1 | * | 8/2001 | Weisburg et al. ............ | 435/6.12 |
| 2002/0137920 | A1 | | 9/2002 | Kleiber et al. | |
| 2002/0166764 | A1 | | 11/2002 | MacPhee | |
| 2003/0059823 | A1 | * | 3/2003 | Matsunaga et al. ................ | 435/6 |
| 2003/0109618 | A1 | | 6/2003 | Parker et al. | |
| 2004/0110222 | A1 | | 6/2004 | Fukushima et al. | |
| 2004/0219066 | A1 | | 11/2004 | Kraus, Jr. et al. | |
| 2005/0100930 | A1 | | 5/2005 | Wang et al. | |
| 2006/0040286 | A1 | * | 2/2006 | Mirkin et al. ..................... | 435/6 |

FOREIGN PATENT DOCUMENTS

| DE | 41 27 657 | 2/1993 |
|---|---|---|
| DE | 100 13 995 | 9/2001 |
| DE | 101 11 520 | 1/2004 |
| WO | 96/41811 | 12/1996 |
| WO | 97/04862 | 2/1997 |
| WO | 98/04584 | 2/1998 |
| WO | 00/47983 | 8/2000 |
| WO | 02/33125 | 4/2002 |
| WO | 2006/122002 | 11/2006 |
| WO | 2007/002567 | 1/2007 |

OTHER PUBLICATIONS

Kenzelmann et al (Genomics (2004) vol. 83, pp. 550-558).*
Akihiko Kondo, Hiroko Kamura, Ko Higashitani; "Development and application of thermo-sensitive magnetic immunomicrospheres for antibody purification", Applied Microbiology and Biotechnology; Springer-Verlag 1994, pp. 99-105.
Masashige Shinkai, Hiroyuki Honda and Takeshi Kobayashi; "Preparation of fine Magnetic Particles and Application for Enzyme Immobilization," *Biocatalysis*, 1991, vol. 5, pp. 61-69.
M.J. Heller et al., "An Active Microelectronics Device for Multiplex DNA Analysis," IEEE Engineering in Medicine and Biology (1996), Mar./Apr., pp. 100-104.
C.F.Edman et al., "Electric field directed nucleic acid hybridization on microchips," Nucleic Acids Research (1997) vol. 25, pp. 4907-4914.
K.A. Peterlinz et al., "Observation of Hybridization and Dehybridization of Thiol-Tethered DNA Using Two-Color Surface Plasmon Resonance Spectroscopy" J.Am.Chem.Soc. 1997, 119, pp. 3401-3402.
Ronald G. Sosnowski et al. "Rapid determination of single base mismatch mutations in DNA hybrids by direct electric field control" *Proc. Natl. Acad. Sci. USA* vol. 94, pp. 1119-1123, Feb. 1997.

* cited by examiner

*Primary Examiner* — Steven Pohnert
(74) *Attorney, Agent, or Firm* — Roberts Mlotkowski Safran & Cole, P.C.; David S. Safran (57) ABSTRACT

A process concentrates nucleic acid molecules to be detected of a sample on a surface, with capture molecules that specifically bind the nucleic acid molecules. A support material has a capture probe that can specifically be linked to the nucleic acid molecules to be detected to give complexes. The support material and the nucleic acid molecules of the sample are incubated to form the complexes. The complexes are moved to the surface. At least one portion of the complexes becomes bound to the capture molecules via the capture probe.

5 Claims, 3 Drawing Sheets

PROCESS FOR CONCENTRATING NUCLEIC ACID MOLECULES

CROSS REFERENCE TO RELATED APPLICATIONS

This application is based on and hereby claims priority to PCT Application No. PCT/EP2008/064876 filed on Nov. 3, 2008 and EP Application No. EP07023377 filed on Dec. 3, 2007, the contents of which are hereby incorporated by reference.

BACKGROUND

The present invention relates to a process for concentrating nucleic acid molecules to be detected of a sample on a surface.

Nucleic acid diagnostics increasingly makes use of "biochips". They are used, for example, for detecting various types and species of nucleic acids, which may be DNA, RNA, cDNA or other nucleic acids. The biochip-based analytical methods usually aim at detecting special nucleic acids in a sample. Thus, for example, a patient's DNA may be examined for the presence of a particular sequence which indicates a predisposition to a disorder. It is likewise possible to detect pathogens such as viruses and bacteria (e.g. HIV, HPV, HCV) in a patient's blood sample by demonstrating the presence of their DNA or RNA in the sample. These analyses have the advantage of increased accuracy over classical immunoassays, since the pathogen is detected directly rather than via antibodies produced against it.

The biochips used are based in their simplest form on a glass substrate on which capture molecules (e.g. oligonucleotides) are immobilized which can specifically bind to the nucleic acid to be detected. These short nucleic acid fragments which are frequently produced synthetically are, with respect to their sequence, at least partially complementary to the sequence of the nucleic acid to be detected, resulting in highly specific binding. Binding of nucleic acids other than the one to be detected must be avoided in any case in order not to obtain a false-positive result. In many methods, actual detection of the nucleic acid takes place by way of fluorescence processes in which a fluorescent dye is attached to the nucleic acid to be detected, for example via biotinstreptavidin binding. After specific hybridization of the nucleic acid with the capture molecules, the biochip is rinsed to remove unbound material. Consequently, the solution does no longer contain any fluorescent dyes. By exciting the dyes, fluorescence can be observed using a CCD camera, making detection possible.

One advantage of biochips is multiplex detection capability. Thus it is possible to immobilize on various positions of the biochip various kinds of capture molecules targeting various nucleic acids to be detected. Detection can then be carried out by way of space-resolved fluorescence measurement. It is therefore also possible to carry out a plurality of detections of nucleic acids in a single process.

The nucleic acids are copied (amplified) prior to detection, since the number of nucleic acid copies present is usually not sufficient for making direct detection possible. The amplification may be carried out, for example, by a polymerase chain reaction (PCR). PCR is based on replicating nucleic acids with the aid of thermostable DNA polymerases. This involves contacting a pair of oligonucleotide primers (single-stranded oligonucleotides) with the nucleic acid to be amplified. The primers are chosen so as to bind at both ends of a fragment to be amplified on the complementary strands. During elongation the primers are then elongated in the 3' direction along the particular target nucleic acid strand (forward and reverse primers). Forward and reverse primers are alternatively also referred to as sense or antisense primers. In this way it is possible to amplify the piece located between the sites on the target nucleic acid that are complementary to the primers. For subsequent detection reactions, the PCR products are advantageously removed from primers, nucleotides and other interfering components of the PCR mixture.

The PCR process comprises a plurality of thermocycles, each of which comprises three steps: the sample is first heated (e.g. to 94° C.) in order to separate the strands of the double-stranded target DNA present in the sample (denaturation). This is followed by lowering the temperature (e.g. to 4560° C.) for the primers to be able to attach to the complementary regions of the now single-stranded DNA (annealing). In the last step, the primers bound to the single strand are extended by DNA polymerase in the 3' direction according to the information of the DNA template strand, with the corresponding nucleoside triphosphates in the solution being used as building blocks (elongation, e.g. at 72° C.). This cycle is typically run approx. 15-50 times during a PCR. The above temperatures are given merely by way of example and should be adjusted to the PCR to be carried out specifically in each case.

It is thus possible to prepare from a few specimens present of a DNA (or generally of a nucleic acid) a multiplicity of copies within a very short time whose concentration is sufficient for subsequent qualitative detection of the DNA or nucleic acid in the sample. For example, 20 PCR cycles (typically taking 20 to 40 minutes) produce theoretically $2^{20}$ times, i.e. about $10^6$ times the amount of the nucleic acid originally used. At the same time, PCR enables a label which makes detection possible to be incorporated into the resulting PCR product. Thus it is possible to use, for example, biotin-labeled PCR primers or nucleoside triphosphates, resulting in the synthesized PCR products being biotinylated. After the PCR product has attached to the immobilized capture molecules, biotin is, as a result, likewise immobilized on the biochip at the corresponding position. In a further step streptavidin-linked fluorescent dyes can then be bound to the biotin, which allow the nucleic acid or its PCR product to be detected. Other detection systems, based on electrochemical detection for example, can be used as an alternative to the fluorescent dye.

A central point in biochip-based detection methods is hybridization, i.e. binding of the nucleic acid to be detected (this term is intended herein to be synonymous with the PCR products produced from the nucleic acids). Sensitivity of nucleic acid detection depends on hybridization efficiency. The nucleic acid is usually incubated with the biochip, thereby enabling hybridization to take place. The latter can be improved by choosing a suitable temperature and buffer medium. It is also important that the nucleic acids are moved to the biochip surface occupied with capture molecules for hybridization to be able to take place. It is therefore not optimal, if movement of the nucleic acid is caused merely by thermal diffusion. Thus, for example, the rate constant is only about $8 \times 10^{-8}$ cm$^2$/s for a 25mer oligonucleotide ("Observation of hybridization and dehybridization of Thiol-tethered DNA using two-color surface plasmon resonance spectroscopy" Peterlinz et al. (1997), J. Am. Chem. Soc. 119 3401-3402), resulting merely in an average migration of 0.096 cm within a hybridization time of sixteen hours. Thus, assuming that the surface is 4 cm$^2$ in size, passive diffusion alone renders only about 1.5% of the sample nucleic acid accessible to hybridization to the capture molecules immobilized on the biochip. A number of active processes can increase hybridization efficiency.

Thus, C. F. Edman et al. disclose in "Electric field directed nucleic acid hybridization on microchips", Nucleic Acids Research (1997) 25, 4907-4914, nucleic acids being moved electrophoretically to the biochip by applying an electric field. Hybridization is rendered substantially faster by concentrating the nucleic acid close to the surface of the biochip than by thermal movement of the nucleic acids alone. It is moreover possible to remove non-hybridized nucleic acids from the biochip surface by reversing the electric potential. The method described requires the electrodes to be specially prepared with a protective layer in order to prevent free radicals and changes in pH occurring during the electrode reaction from damaging the concentrated nucleic acids. M. J. Heller et al. disclose a comparable method in "An Active Microelectronics Device for Multiplex DNA Analysis", IEEE Engineering in Medicine and Biology (1996) March/April, 100-104.

A multiplicity of methods in biochemistry and medical diagnostics now make use of magnetic, polymeric support materials, in particular polymeric particles, for simplifying the removal of cells, proteins and nucleic acids. Compared with conventional separation methods, using magnetic support materials is advantageous in that the loaded support materials can readily and rapidly be removed from the other components of a sample with the aid of magnetic forces. Magnetic bead-shaped or spherical polymeric particles based on polyvinyl alcohol with a narrow particle size distribution within a range of less than 10 μm have proved particularly suitable for such separation methods (WO 9704862).

It is also known that particular biological materials, in particular nucleic acids and proteins, can be isolated from their natural environment only with increased efforts. This is especially due to the fact that mechanical, chemical and biological cell lysis processes must be utilized for isolating the nucleic acids and proteins from the nucleus or the cell membrane or organelles. In addition, the corresponding biological samples usually comprise further, solid and/or dissolved compounds such as other proteins and components of the cytoskeleton, which can impair isolation. An additional difficulty is the fact that very often only small concentrations of the nucleic acids or proteins are present in the biological sample to be studied.

In order to be able nevertheless to utilize the advantages of using magnetic particles for isolating nucleic acids from biological samples, it has been proposed inter alia to isolate nucleic acids with the aid of magnetic particles having a glass surface which is essentially pore-free (WO 9641811). These particles must have a particular composition, i.e. their glass surface must have a particular composition, in order to achieve the desired efficacy. Preparation of these particles moreover requires a relatively complicated process to achieve the necessary sintering of the glass surface.

Known diagnostic processes, for example from nucleic acid and protein diagnostics, usually require a multiplicity of manual operations in order to arrive at an analytical result. This requires inter alia separation of the components to be detected from the rest of the sample. Known examples of separation methods are filtration, centrifugation, chromatography and extraction. All of these are chemical and physical separation processes which are usually not suitable for sequence-specific isolation of DNA or proteins from the sample. Use is made, for example, of resins whose surfaces are functionalized so as to be able to bind DNA or proteins. These target molecules are purified by binding to the solid phase of the resin, followed by a plurality of washing steps and subsequent detachment of the target molecule from the solid phase under suitable buffer conditions. The target molecule must be bound tightly, while contaminating components of the sample are dissolved in a different, liquid phase. After various washing procedures, the target molecule must then be detached again from the solid phase, for example by changing the liquid phase. The repeated change of medium is firstly very costly with regard to material, and secondly product yields fluctuate with each additional process step, making quantitative calibration difficult. In particular in integrated analytical processes, for example lab-on-a-chip systems in which the samples are prepared and analyzed essentially automatically, checking the individual process steps is often not possible, and as a result deviations in the individual process steps amplify each other and may lead to large deviations in the analytical result.

Individual steps can be simplified or even automated completely by the described support particles, also referred to as magnetic beads. The magnetic beads are provided with affinity ligands or other surface modifications and are therefore suitable for binding particular biomolecules, for example DNA, from a solution to their surface. A purification process typically involves adding a suspension of magnetic beads to the sample to be separated in a test tube. After an incubation time of several minutes to enable the affinity ligand to bind to the desired biological molecule, a magnetic field is applied, which removes the particles by accumulating them on one tube wall. The supernatant is discarded and the particles are then washed at least once. For this purpose, the magnetic field is removed first and the particles are suspended in a fresh buffer solution which contains mostly chaotropic salts which prevent the biomolecules from detaching from the support material. The magnetic beads are then deposited on the vessel wall by reapplying the magnetic field. Thus it is possible, after several washing steps, to eluate the molecules by a low salt buffer solution which removes the bound biomolecules from the magnetic beads, in a solution which is free of interfering components, in contrast to the crude extract. The magnetic beads are deposited again on the vessel wall, making available the bio-molecules in the supernatant solution. A disadvantage of the process described is the large amount of liquid required in each case, in the range of several hundred microliters for each individual process step.

Eukaryotic or prokaryotic cells or viruses are known to be isolated, by way of example, by coupling specific antibodies to a fluorescent marker or magnetic beads. The antibody is usually monoclonal and directed to specific binding sites, for example to a surface receptor molecule of a corresponding antigen of the cell or the virus. The desired cells or viruses are labeled by coupling the antibodies to the particular binding site and sorted, for example, by FACS or a permanent magnet. The sorting process can be carried out firstly by way of "positive selection", involving further processing of the labeled cells or viruses. Secondly, a "negative selection" may be carried out, involving removal of the labeled cells and further processing of the remaining cells. Both methods enable the cells or viruses to be quantified and, as a result, the amounts of reagents required for the further processing to be calculated.

DE 101 11 520 B4 discloses a process for purifying biomolecules with the aid of magnetic particles, which enables in particular relatively small amounts of liquid to be purified in an essentially automated manner. It describes the suspension with magnetic particles being passed through a pipeline which passes by a strong magnetic field. With suitable settings of diameter, flow rate and magnetic field strength, the magnetic particles are deposited on the wall of the pipeline when passing through. The supernatant is discarded by emptying the pipeline or is collected in a receptacle. The arrested particles can then be washed by rinsing with washing solutions. During the washing procedure, the magnetic particles may be held in the pipeline or be suspended and deposited again. The biomolecules are detached from the magnetic particles of the suspension by rinsing with a suitable buffer solution. The pipeline here should be de-signed in such a way that small amounts of liquid of less than 50 μl can also be handled. The described process is particularly suitable for purifying DNA or RNA. The DNA or RNA available in solution at the end of the process may be introduced automatically to a corresponding analytical system. Automation may be carried out by way of a pipetting robot. If the DNA is to be detected via sequence-specific hybridization, it is moreover suggested to run the pipeline additionally over a heating element to achieve denaturation of the DNA double strand. However, in order to analyze DNA using the described process, it is still necessary to extract the DNA from the sample by process steps which have not been described.

Magnetic beads are not only suitable for purifying samples but can also be used for other purposes. Thus, US 2004/0219066 A1 describes a device, by which various particles can be sorted. The particles are bound to different magnetic beads having different magnetic momentums. A magnetic field gradient which moves the magnetic beads, due to their different magnetic momentums, into different collecting boxes is generated in a process chamber. The various particles can thus be distinguished by the differently designed magnetic beads.

WO 00/47983 describes an electrochemical biosensor in which magnetic beads are linked via affinity ligands to components of a sample. An enzyme is coupled to the bound components of the sample and an added substrate is cleaved by the enzyme. The substrate gives rise to a molecule which can be subjected to a redox cycling process. The particular component of the sample can be detected in this way.

Moreover, paramagnetic magnetic beads are known to be used for detecting DNA. Here, capture molecules complementary to the DNA to be detected are located on a magnetorestrictive sensor. If the sample studied contains the DNA to be detected, hybridization between the DNA to be detected and the capture molecules takes place. The hybridized DNA has been or is labeled with biotin to which streptavidin-coated magnetic beads couple. The biotin label is usually introduced into the DNA to be detected by an upstream PCR utilizing bio-tin-labeled primers or nucleotides. After coupling to the paramagnetic beads, the latter are magnetized by an applied magnetic field and their stray field is measured by the magnetoresistive sensor. This results indirectly in quantitative detection of the DNA in the sample.

DE 41 27 657 and WO 9704862, whose disclosure with regard to the methods of preparing support materials is hereby incorporated as reference, disclose processes for preparing magnetic polyvinyl alcohol support materials, preferably in bead-like particle design. According to the disclosed processes, magnetic particles can be prepared with a very narrow particle size distribution and with particle sizes of from 1 to 4 μm, as used in particular for isolating biosubstances in suspension and for diagnostic medicine.

The polyvinyl alcohol particles are prepared by adding particular emulsifier mixtures to the oil phase of the water-in-oil emulsion. Suitable emulsifiers which are added as additives to the oil phase are propylene oxide-ethylene oxide block copolymers, sorbitan fatty esters, mixed complex esters of pentaerythrite fatty esters with citric acid, polyethylene glycol-castor oil derivatives, block copolymers of castor oil derivatives, polyethylene glycols, modified polyesters, polyoxyethylene sorbitan fatty esters, polyoxyethylene-polyoxypropylene-ethylenediamine block copolymers, polyglyceryl derivatives, polyoxyethylene alcohol derivatives, alkylphenyl-polyethylene glycol derivatives, polyhydroxy fatty acid-polyethylene glycol block copolymers, polyethylene glycol ether derivatives. Substances of this kind are commercially known inter alia under the trade name: Pluronic®, Synperonic®, Tetronic®, Triton®, Arlacel®, Span®, Tween®, BrijOR, ReneXOR, Hyperme®, Lameform®, Dehymuls® or Eumulgin®.

To obtain uniform, bead-shaped polymeric particles, preferably with particle sizes of 0.5-10 μm, a mixture of at least two, preferably three to four, of the surfactants is added to the oil phase. Preference is given to mixing a lipophilic emulsifier component with at least one emulsifier which has semihydrophilic properties, i.e. which is soluble in both water and oil. Examples of emulsifiers which meet the latter properties are: ethylene oxide-propylene oxide block copolymer derivatives with a predominant ethylene oxide proportion, polyethylene glycol hexadecyl ethers, shorter-chain polyoxyethylene sorbitan fatty esters, polyethylene glycols or shorter-chain sorbitan fatty esters. The concentration of the emulsifiers in the oil phase is usually 2-6% by volume, preferably 3.5-5.0% by volume. Advantageous with respect to fineness and narrow particle size distribution of polymer droplets are those emulsifier mixtures which comprise at least two lipophilic components and one semihydrophilic emulsifier. The concentration of the semihydrophilic emulsifier is usually between 15 and 30% by volume, based on the total amount of emulsifier. In addition to fineness of the particles, the particles show a bead-like shape.

Apart from the emulsifiers for the oil phase, special surfactants which are soluble in the aqueous polymer phase also contribute to improving the quality of the emulsion, especially of polyvinyl alcohol solutions with low molecular weight (Mowiol, Clariant GmbH, Frankfurt am Main, Del.). In addition, the magnetic colloids added in solid form are successfully finely dispersed by adding ionic emulsifiers. Examples of such emulsifiers which can also be used as binary mixtures are: serum albumin, gelatin, aliphatic and aromatic sulfonic acid derivatives, polyethylene glycols, poly N-vinylpyrrolidone or cellulose acetate butyrate. The amounts of emulsifiers used are usually 0.01-2% by weight, based on the polymer phase, with the concentration of the ionic emulsifiers always being between 0.01 and 0.05% by weight. The skilled worker is familiar with influences of stirrer speeds and of concentrations and viscosities of the two phases on particle size. To obtain the preferred particle sizes of 0.510 μm, stirrer speeds of 1500-2000 revolutions per minute are required, with conventional two blade propeller stirrers being used.

In principle, those ferro- or superparamagnetic colloids which have an appropriate particle size and normally a magnetic saturation of from 50 to 400 Gauss may be used as magnetic particles which are encapsulated into the polyvinyl alcohol matrix during the process. Another requirement to be met by the magnetic particles is dispersibility in the aqueous polymer phase containing the polyvinyl alcohol. During subsequent emulsion in the organic phase, the magnetic colloids are then simultaneously enclosed in the polymer droplets.

Suitable magnetic colloids are preferably magnetites with particle sizes of 10-200 nm. Such substances can be obtained commercially, for example, under the trade name Bayferrox or Ferrofluidics. Since preparing such colloids is general related art, the magnetic particles may also be prepared by the disclosed processes, as described, for example, by Shinkai et al., Biocatalysis, Vol. 5, 1991, 61, or Kondo et al., Appl. Microbiol. Biotechnol., Vol. 41, 1994, 99. The concentrations of the colloids in the polymer phase are, in each case based on this phase, usually between 4 and 14% by volume for colloids which are already aqueous colloids due to their preparation, and 0.3-2% by weight for solid substances. Preparation involves admixing the magnetic colloids directly with the polymer phase. In order to ensure a finely dispersed, even distribution of the particles, brief mixing of the aqueous dispersion by a high revolution dispersing tool (Ultra-Turrax) with subsequent ultrasound treatment is beneficial. The polymer phase required for preparing the magnetic particles usually includes a 2.5-10% by weight polyvinyl alcohol solution.

The magnetic polyvinyl alcohol support material can then be obtained from the suspension by methods known per se to the skilled worker, for example by filtration and washing.

A known process for functionalization comprises equipping the support material with affinity ligands on the surface. This usually requires attaching chemically reactive groups on the surface, to which the affinity ligands are then bound. These groups may be, for example, tosyl, hydroxyl, aldehyde or carboxyl, amino, thiol or epoxy groups. They may generally be provided by treating uncoated monodisperse superparamagnetic particles in order to provide them with a surface layer of a polymer carrying such a functional group, for example a cellulose derivative or a polyurethane together with a polyglycol for providing hydroxyl groups, a polymer or copolymer of acrylic acid or methacrylic acid for providing carboxyl groups or an amino-alkylated polymer for providing amino groups. U.S. Pat. No. 4,654,267 discloses a plurality of surface coatings.

DE 100 13 995 A1 discloses magnetic support materials based on polyvinyl alcohol, whose surface is at least partially silanized and, where appropriate, equipped with biomolecule-coupling affinity ligands. The described support materials may be designed as filter, membrane or particle. Preference is given to the magnetic support material being bead-shaped or spherical particles, the particles having a particle size preferably of from 0.2 to 50 μm, particularly preferably from 0.5 to 5 μm. Aside from the preferably bead-shaped and spherical design of the particles, their particle size distribution should be within as narrow a range as possible. The support materials are preferably prepared in particle form by reacting the polyvinyl alcohol support material with an organic silane compound. The silanized particles are then reacted with affinity ligands.

Affinity ligands which may be coupled are in principle any ligands used in affinity chromatography. Examples of these are: protein A, protein G, protein L, streptavidin, biotin, heparin, antibodies, serum albumin, gelatin, lysine, concanavaline A, oligosaccharides, oligonucleotides, polynucleotides, protein-binding metal ions, lectins, aptamers or enzymes. The special fractionations which can be carried out using such affinity matrices are general related art.

The described advantages of the magnetic beads can also be used for concentrating nucleic acids on biochips, as disclosed by US 2002/0166764 A1. The device described there comprises a biochip which is arranged in a chamber. A liquid flow can be adjusted through the chamber. Outside the chamber, there is a magnetic field generator which enables magnetic beads inside the chamber to be moved to the surface of the biochip. The nucleic acids are specifically linked to the magnetic beads before introduction into the chamber. The linkage is provided by oligonucleotides on the magnetic beads. The magnetic beads, and therefore also the nucleic acids, are then moved in the chamber by the magnetic field generator to the surface of the biochip and held there. The presence of the nucleic acids on the magnetic beads is detected by a redox cycling process. The described process is not capable of multiplexing, since the magnetic beads cannot be addressed to individual positions, as required in microarrays. The magnetic beads are held unspecifically close to the surface of the biochip.

WO 98/4584 discloses a process for detecting proteins (immunoassays), which likewise makes use of magnetic beads. A capture molecule capable of coupling to a target binding molecule is immobilized on a magnetic bead. The target binding molecule in turn is linked to the protein to be detected. After a complex of the protein, the target binding molecule, the capture molecule and the magnetic bead has formed, it can be separated from the rest of the sample by magnetic forces. Under "mild" conditions which are not specified in any detail, the bond between the capture molecule and the target binding molecule can be dissolved, without the target binding molecule losing its binding ability. The magnetic beads with the capture molecules remaining thereon are removed. The proteins are bound by immobilized antibodies on a surface and are therefore likewise immobilized. Detection molecules, for example fluorescent dyes, are bound to the target binding molecules for detection. Thereby the proteins in the sample can be detected.

SUMMARY

It is one potential object to provide an improved process for concentrating nucleic acids on biochips.

The inventors propose a first process for concentrating nucleic acid molecules to be detected of a sample on a surface, with capture molecules that specifically bind a capture probe being immobilized on the surface. The process comprises:
  providing a support material which has the capture probe and can specifically be linked to the nucleic acid molecules to be detected to give complexes which comprise the support material and the nucleic acid molecules,
  incubating the support material with the sample and forming the complexes,
  moving the complexes to the surface,
  binding at least one portion of the complexes to the capture molecules by the capture probe.

The process has the advantage of using the capture probe and linking it with the immobilized capture molecules on the surface of the biochip enabling the magnetic beads to be efficiently linked to the capture molecules. As a result, the nucleic acid to be detected is immobilized close to the surface and can be detected by known processes. In addition, the biochip is not specific for nucleic acids and can therefore be used universally. Specificity is caused only by the design of the support material which firstly comprises the sample-independent capture probe for selective (generically selective (addressable)) binding to the surface and which secondly is capable of binding specifically the nucleic acid to be detected. Thus it is possible in sample preparation to mix a nucleic acid to be detected with appropriate designed support materials and to incubate it with the biochip. The biochip itself can be mass-produced always in an identical manner and used without modification for any detection of various nucleic acids. While nucleic acids form the generically active part (which binds to the capture molecules immobilized on the chip surface) of the support material, the target molecule-specific part may comprise nucleic acids, proteins or aptamers.

The process can be parallelized in a simple manner, i.e. is capable of multiplexing. This requires a plurality of types of support materials with various capture probes which can in each case be linked to different nucleic acids to be detected to give various complexes. The various nucleic acids can therefore be arrested at various sites of the biochip by capture molecules which are immobilized over various sites of the biochip and which are directed against the various capture probes. Known detection processes enable the nucleic acids to be detected in a space-resolved manner.

In an advantageous embodiment, unbound complexes are moved away from the surface and then moved again to the surface. This is followed by binding of at least one further portion of the complexes to the capture molecules. This addresses the problem of the support material with the immobilized nucleic acids usually being distributed evenly on the surface of the biochip, due to moving by the magnetic field. It is thus possible, in particular in multiplex processes, for nucleic acids at measurement locations (spots) of the biochip, at which they do not find any immobilizing partner in the form of capture molecules, to be redistributed. The dimensions of a spot are usually small compared to the entire surface of the biochip. By repeating the process steps several times, hybridization efficiency can be increased, since the complexes which have not yet hybridized are again moved to the surface and partly bound there.

In an advantageous development of the process, the support material surface on which the capture probes and transfer molecules which bind the nucleic acid molecules are immobilized. A support material of this kind can readily be produced by the processes described previously. Highly specific binding of only the selected nucleic acid for each species of the support material provides a high degree of error reliability.

In an advantageous development of the process, the capture molecules, the capture probe and the transfer molecules are nucleic acids. In this way it is possible to generate in a simple manner highly specific binding events required by the process.

The inventors also propose an alternative solution to the problem. Specifically, the inventors propose a second process for concentrating nucleic acid molecules to be detected of a sample on a surface, with capture molecules that specifically bind the nucleic acid molecule being immobilized on the surface, which process comprises:
  providing a support material which can specifically be linked to the nucleic acid molecules to be detected to give complexes which comprise the support material and the nucleic acid molecules,
  incubating the support material with the sample and forming the complexes,
  moving the complexes to the surface,
  separating the nucleic acid molecules from the support material, and
  binding at least one portion of the nucleic acid molecules to the capture molecules.

A particular advantage of this process is the fact that the portion of the nucleic acid molecules is bound to the surface with high efficiency, since moving the complexes to the surface results in their concentration. Moreover, in comparison with the first process, the additional capture probe can be dispensed with. However, the abovementioned advantages over known processes are identical. The specificity of the detection process in this embodiment is in the biochip itself due to the capture molecules immobilized on the surface.

In an advantageous embodiment of the process, the nucleic acid molecules to be detected are separated from the support material and the latter is removed from the surface. This can prevent a possible influence of the support material on subsequent process steps such as, for example, detection of the nucleic acid. The nucleic acid itself here remains immobilized to the capture molecule on the surface of the biochip.

In advantageous embodiments of the process, the support material is in the form of magnetic beads whose surface has transfer molecules for binding the nucleic acid. It is also possible for the chip-bound capture molecules and the transfer molecules to be in the form of nucleic acids.

In an advantageous embodiment, the process further comprises the following steps:
  the capture molecules in each case comprise a nucleic acid sequence which is partially complementary to the nucleic acid sequence of the nucleic acid molecule to be detected,
  the transfer molecules comprise in each case a nucleic acid sequence which is partially complementary to the nucleic acid sequence of the nucleic acid molecule to be detected, and
  the nucleic acid sequences of capture molecules and transfer molecules, which are complementary to the nucleic acid molecules to be detected, are chosen in such a way that the melting temperature of a nucleic acid molecule-transfer molecule hybrid is lower than the melting temperature of a nucleic acid molecule-capture molecule hybrid.

This embodiment of the capture and transfer molecules provides a simple possibility of separating the complex. The partially complementary nucleic acid sequences are usually contiguous. Different melting temperatures of the hybrids can be achieved in a simple manner via the length of the complementary nucleic acid sequences. This ensures that when the linkage between transfer molecule and nucleic acid is dissolved, the linkage between the nucleic acid molecule and the capture molecule remains intact and the nucleic acid molecule is still immobilized. The support material can thus be removed in a simple manner. In general, any modifications of stringency conditions can be used for separation. Thus it is possible, for example, to modify the stringency conditions by changing the salt concentration or the formamide content.

Accordingly, an advantageous embodiment of the process comprises incubating under stringency conditions which are below melting (denaturation) of the nucleic acid molecule-transfer molecule hybrids. The complexes are moved to the surface under stringency conditions which are below melting of the nucleic acid molecule-transfer molecule hybrids.

An advantageous embodiment of the process comprises incubating at a first temperature which is below the melting temperature of the nucleic acid molecule-transfer molecule hybrids. The complexes are moved to the surface at a second temperature which is below the melting temperature of the nucleic acid molecule-transfer molecule hybrids. After binding of the complexes to the capture molecules, the temperature is increased to a third temperature which is between the melting temperatures of the nucleic acid molecule-transfer molecule hybrids and the nucleic acid molecule-capture molecule hybrids. This ensures that the linkage between the nucleic acid and the capture molecules remains intact, while the linkage between the nucleic acid molecule and the transfer molecule is severed.

The described process and the advantageous developments can readily be parallelized. It is merely necessary to equip various sites of the biochip with various capture molecules which are partially complementary to various nucleic acids to be detected. It is also necessary to provide various support materials having different transfer molecules which then transport the various nucleic acids to the surface. Depending on the nucleic acids to be detected it is alternatively also possible to use magnetic beads of the same kind, all of which are capable of binding any of the nucleic acids to be detected.

This is possible because immobilization to the surface of the biochip is highly specific due to the capture molecules located there.

The inventors also propose a process for concentrating different nucleic acid molecules to be detected of a sample on a surface, with capture molecules that specifically bind the nucleic acid molecules being immobilized in groups and at different sites on the surface (201), which process comprises:
- providing a support material which can specifically be linked to the nucleic acid molecules to be detected to give complexes which comprise the support material and the nucleic acid molecules,
- incubating the support material with the sample and forming the complexes,
- moving the complexes to the surface,
- separating the nucleic acid molecules from the support material, and
- binding at least one portion of the nucleic acid molecules to the capture molecules.

This multiplex process can be implemented particularly readily, since only one type of support materials with binding properties for the different nucleic acids is required.

Otherwise the same advantageous developments of the process, as described above, can be implemented.

BRIEF DESCRIPTION OF THE DRAWINGS

These and other objects and advantages of the present invention will become more apparent and more readily appreciated from the following description of the preferred embodiments, taken in conjunction with the accompanying drawings of which

DETAILED DESCRIPTION OF THE PREFERRED EMBODIMENT

Reference will now be made in detail to the preferred embodiments of the present invention, examples of which are illustrated in the accompanying drawings, wherein like reference numerals refer to like elements throughout.

The exemplary embodiments described hereinbelow refer to processes for concentrating DNA molecules. They can be applied in principle in the same manner to any nucleic acids. It is likewise possible to concentrate other biomolecules for which specific binding partners are available by the processes described. The processes are depicted by way of example for a few or only one specimen of nucleic acids. Usually a large number of specimens is used in order to enable the nucleic acids to be detected subsequently.

Figure 1:
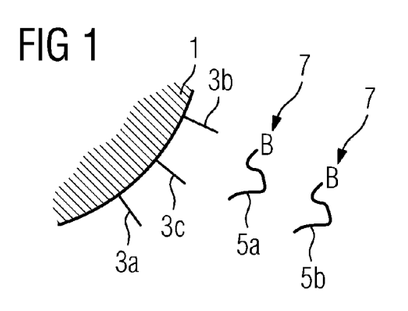
FIGS. 1 to 10 depict various process steps of a hybridization process.

FIG. 1 depicts diagrammatically a magnetic bead 1 which has three different oligonucleotides, 3a, 3b, 3c, as transfer molecules. Two different DNA molecules to be detected, 5a and 5b, are likewise depicted. The oligonucleotides 3a and 3b have sequences that are partially complementary to the DNA molecules 5a and 5b. The DNA molecules 5a and 5b bear in each case a biotin molecule 7. The situation in FIG. 1 represents the start of an incubation phase of the process.

The DNA molecules 5a and 5b have been isolated, purified and, where appropriate, amplified by known processes, for example, from a blood sample of a patient prior to the incubation phase. Isolation and purification, however, are also possible by the process below itself. Only a possibly necessary lysis is required beforehand in order to release the DNA molecules 5a and 5b from the corresponding cells or viruses.

Figure 2:
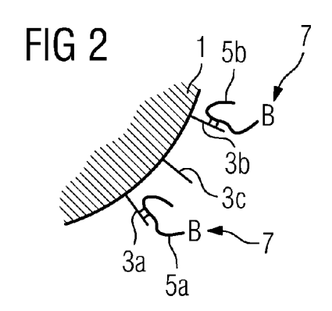

In FIG. 2, incubation of the magnetic bead 1 with the DNA molecules 5a and 5b has finished. The DNA molecules 5a and 5b have bound to the oligonucleotides 3a and 3b, respectively, and are thus immobilized on the magnetic bead 1. Binding of the DNA molecule 5a with the oligonucleotide 3a is indicated symbolically by two connecting lines. The connecting lines symbolize an overlapping complementary nucleic acid sequence of the DNA molecule 5a and the oligonucleotide 3a. Binding between the DNA molecule 5b and the oligonucleotide 3b is depicted in a similar manner.

Figure 3:
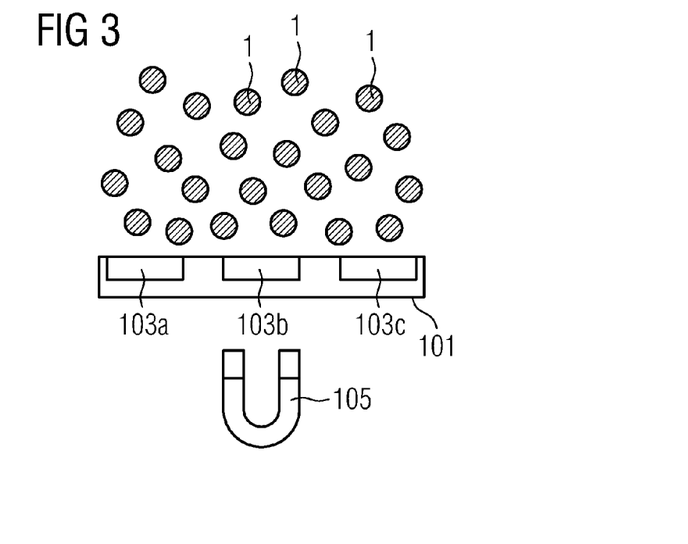

FIG. 3 depicts diagrammatically the surface of a biochip 101. The biochip 101 comprises three sensor fields, 103a, 103b and 103c, which are equipped for detecting various DNA molecules. A magnetic field generator 105 is provided for (depicted only diagrammatically here). It may be designed, for example, as a movable permanent magnet or as a coil. The biochip 101 is located in a reaction chamber (not shown) which is filled with a solution. The solution comprises the incubated magnetic beads 1 in a concentration $C_1 = n_1/V_1$, where $n_1$ is the number of magnetic beads 1 and $V_1$ is the volume of the solution.

Figure 4:
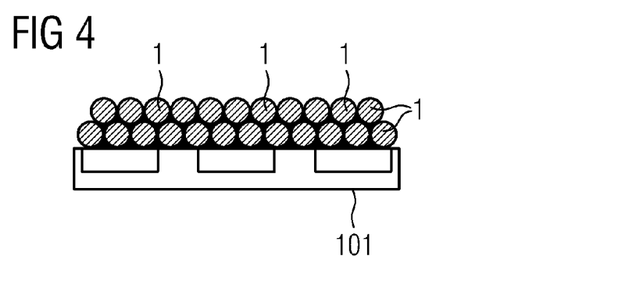

FIG. 4 depicts the biochip 101 after applying a magnetic field through the magnetic field generator 105. The magnetic beads 1 have been moved through the magnetic field to the surface of the biochip 101 and are present there in a concentration $C_2 = n_1/V_2$, wherein $V_2$ is the volume above the biochip 101 in which the magnetic beads 1 are now concentrated. The concentration $C_2$ is higher than $C_1$ because $V_2 \ll V_1$. Thus the magnetic beads 1 have been concentrated close to the surface of the biochip 101.

Figure 5:
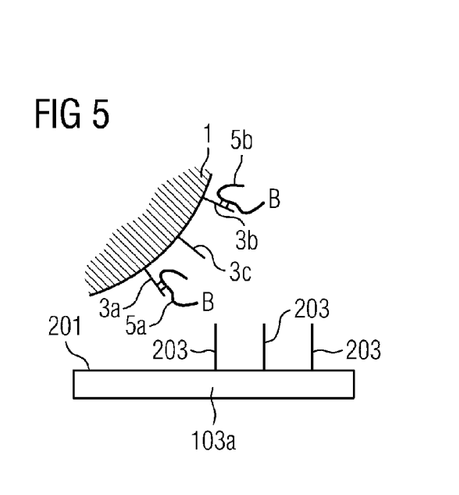

FIG. 5 depicts a section of the situation on the surface 201 of the sensor field 103a. Capture molecules which are oligonucleotides 203 are immobilized on the sensor field 103a. Like the oligonucleotides 3a, they are directed to the DNA molecule 5a, albeit to a different subsequence.

Like the oligonucleotide 3a, the oligonucleotide 203 has a subsequence which is complementary to the DNA molecule 5a. This subsequence, however, is longer than the complementary subsequence of the DNA molecule 5a and of the oligonucleotide 3a. The DNA molecule 5a bound to the magnetic bead 1 is incubated with the surface 201 of the sensor field 103a at a temperature $T_1$ which is below the melting temperature of the hybrid of the DNA molecule 5a and the oligonucleotide 3a. This hybrid thus will remain stable at the present temperature $T_1$. Since the complementary subsequences have different lengths, the DNA molecule 5a tends to form a hybrid with the oligonucleotide 203 at the temperature $T_1$. The melting temperature of the hybrids formed thereby is above the melting temperature of the hybrid of the DNA molecule 5a and the oligonucleotide 3a.

Figure 6:
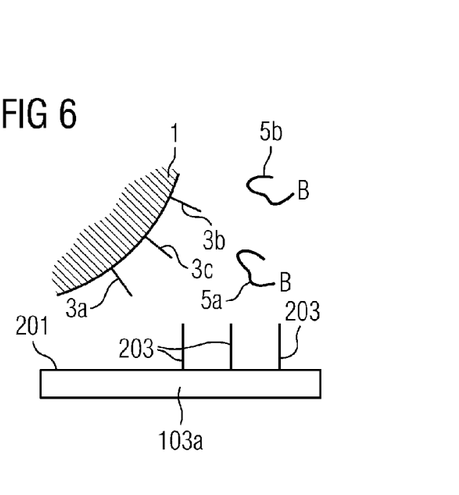

FIG. 6 depicts the situation on the surface 201 of the sensor field 103a after splitting of the complexes of the magnetic bead 1 and the DNA molecule 5a and 5b, respectively.

Splitting of the complexes has been achieved by increasing the temperature to a temperature $T_2$. The chosen temperature $T_2$ is above the melting temperature of the hybrids of the DNA molecules 5a and 5b and the oligonucleotides 3a and 3b, respectively. Increasing the temperature to the temperature $T_2$ results in the hybrids being dissolved, so that the magnetic bead 1 with the oligonucleotides 3a immobilized thereto is dissolved from the DNA molecule 5a.

Increasing the temperature to the temperature $T_2$ has likewise dissolved the hybrid between the DNA molecule 5b and the oligonucleotide 3b, and as a result the DNA molecule 5b is again free in solution, independently of the magnetic bead 1.

Figure 7:
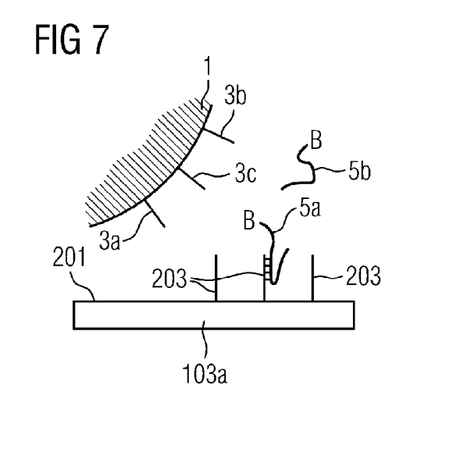

The temperature $T_2$ is below the melting temperature of the hybrids of the DNA molecule 5a and the oligonucleotide 203, and the hybrid is therefore stable at the chosen temperature $T_2$. FIG. 7 depicts the surface 201 after hybridization of the DNA molecule 5a with the oligonucleotide 203. The linkages of the DNA molecule 5a to the oligonucleotide 203 are symbolized by four connecting lines. The DNA molecule 5b which was likewise immobilized on the magnetic bead 1 does not find any binding partner in the oligonucleotides 203 on the surface 201 of the sensor field 103a, resulting in no linkage in this case.

If the DNA molecule 5b is intended to be detected likewise, corresponding oligonucleotides must be immobilized on a separate sensor field (for example on the sensor field 103b), where the DNA molecule 5b can then be bound by a complementary subsequence of the oligonucleotides immobilized there. Accordingly, the DNA molecule 5a does not find a binding partner in the sensor field 103b.

After the magnetic field has been switched off, the magnetic beads 1 will be free in solution again, so that the surface 201 of the sensor field 103a is no longer occupied with magnetic beads 1. This situation corresponds to that of FIG. 3, apart from the previously hybridized DNA molecule 5a. Interference with the subsequent detection reaction of the DNA molecule 5a is therefore ruled out.

It can be assumed that random uniform distribution of the magnetic beads 1 on the entire surface of the biochip 101 did not succeed in immobilizing enough specimen of the DNA molecule 5a to the surface 201 of the sensor field 103a. According to uniform distribution, the magnetic beads 1 with the DNA molecules 5a are evenly distributed on the surface after the magnetic field has been switched on. FIG. 7 demonstrates this by the fact that here the DNA molecule 5b is present above the sensor field 103a and not, as ultimately desired, at the sensor field 103b. Accordingly, magnetic beads 1 with further copies of the DNA molecule 5a will be present on the surfaces of other sensor fields of the biochip or in between. By repeating the abovementioned process steps, further specimen of the DNA molecule 5a can be moved to the surface 201 of the sensor field 103a. At the temperature $T_2$ and with the magnetic field switched off, the magnetic beads and the DNA molecules 5a and 5b which are not yet immobilized on a sensor field are again in solution with a volume $V_1$. By lowering the temperature again to the temperature $T_1$ which, as above, is below the melting temperatures of the hybrids of DNA molecule 5a and oligonucleotide 3a, DNA molecules 5a and 5b which are free in solution are again immobilized on magnetic beads 1. This process is efficient, since a large concentration of magnetic beads 1 has been added and therefore a sufficient number of hybridization partners for the DNA molecules 5a and 5b are available. The probability of the DNA molecules 5a and 5b finding a hybridization partner within a short time is sufficiently high. Switching on the magnetic field again moves the magnetic beads 1 with the DNA molecules 5a and 5b again immobilized thereto again to the surface of the biochip, where they are concentrated in a distinctly smaller volume $V_2$, corresponding substantially to the situation of FIG. 4.

Figure 8:
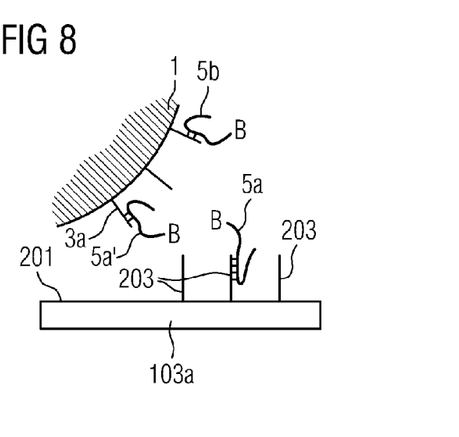

FIG. 8 depicts this situation. The DNA molecule 5a which has been moved to the surface 201 of the sensor field 103a in the previous procedure is still linked to one of the oligonucleotides 203 and therefore immobilized on the surface 201. On the magnetic bead 1, a DNA molecule 5a' which is identical to the DNA molecule 5a is now again bound to the oligonucleotide 3a and can now hybridize with another one of the oligonucleotides 203. As in the first process cycle, this process is efficient because the DNA molecule 5a' is concentrated close to the surface 201.

Figure 9:
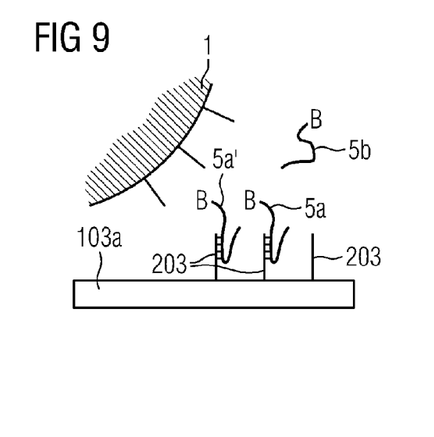

After hybridization of the DNA molecule 5a' with the oligonucleotide 203, the temperature is again raised to a temperature $T_2$ above the melting temperature of the hybrids of the DNA molecule 5a' and the oligonucleotide 3a, and as a result the magnetic beads detach from the DNA molecule 5a. This is shown in FIG. 9. The process described can be repeated any number of times so that concentration of the DNA molecules 5a and 5b on the corresponding sensor surfaces is carried out efficiently.

Figure 10:
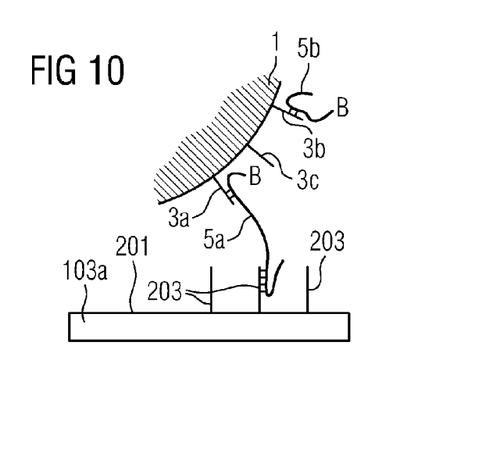

It is likewise possible, in the situation in FIG. 5, that the DNA molecule 5a hybridizes with the oligonucleotide 203 before the DNA molecule 5a is separated from the magnetic bead 1. This is depicted in FIG. 10. Increasing the temperature to the temperature $T_2$ results in the same situation as in FIG. 7. The hybrids of the DNA molecule 5a and the oligonucleotide 3a have melted, while the hybrid of the DNA molecule 5a and the oligonucleotide 203 is stable. A corresponding process has the following steps:

binding at least one portion of the nucleic acid molecules to the capture molecules providing a support material which can specifically be linked to the nucleic acid molecules to be detected to give complexes which comprise the support material and the nucleic acid molecules, incubating the support material with the sample and forming the complexes, moving the complexes to the surface, and binding at least one part of the complexes to the capture molecules.

The process described on the basis of FIGS. 1 to 10 uses magnetic beads 1 with in each case different oligonucleotides, 3a, 3b and 3c, on the surface. This has the advantage that only one species of magnetic beads 1 needs to be used, while it is still possible to carry out a multiplex process. In an alternative exemplary embodiment it is possible to immobilize in each case one species of oligonucleotides 3a, 3b or 3c for only one binding partner (DNA molecule 5a or 5b) on a magnetic bead 1, thereby generating different species of magnetic beads 1. This is firstly required, if only one species of DNA molecules is to be detected. Here too, however, the process can be parallelized by adding different species of magnetic beads 1 having on their surface in each case one type of oligonucleotide 3a, 3b or 3c. Thus it is possible, for example, to stock a multiplicity of various types of magnetic beads 1 which are in each case coated with one type of oligonucleotides, 3a, 3b or 3c, and to mix them in a reaction mixture according to the DNA molecules to be detected, 5a or 5b.

Figure 11:
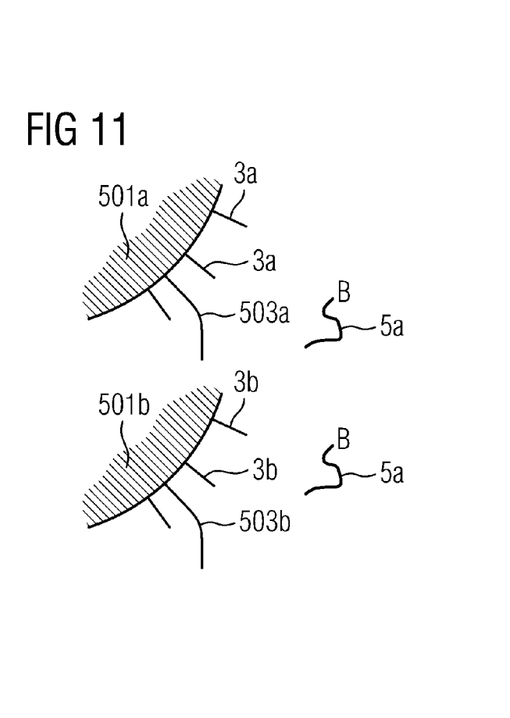
FIGS. 11 to 13 depict various process steps of an alternative hybridization process.
Figure 13:
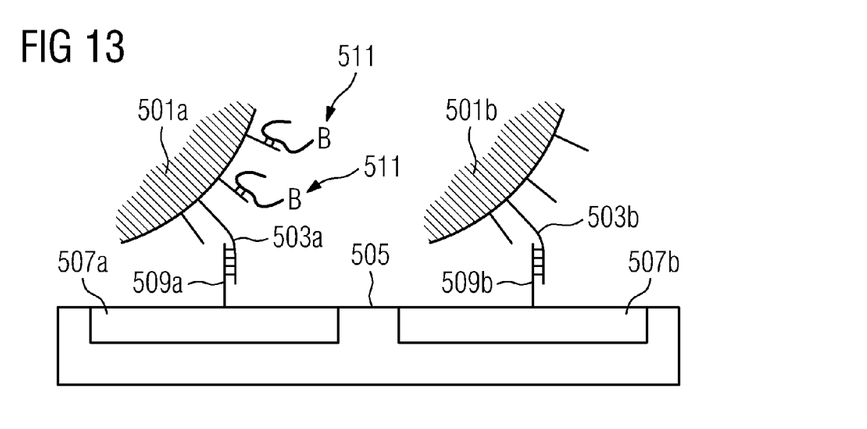

FIG. 11 depicts an alternative exemplary embodiment. Two magnetic beads, 501a and 501b, are depicted which in each case carry one species of oligonucleotides 3a and 3b. The oligonucleotide 3a is directed to a DNA molecule 5a which is present in the solution. The oligonucleotide 3b is directed to a DNA molecule which is not present in the solution. Moreover, further oligonucleotides 503a and 503b are immobilized on the surfaces of the magnetic beads 501a and 501b. FIG. 13 illustrates the function of the oligonucleotides 503a and 503b.

Figure 12:
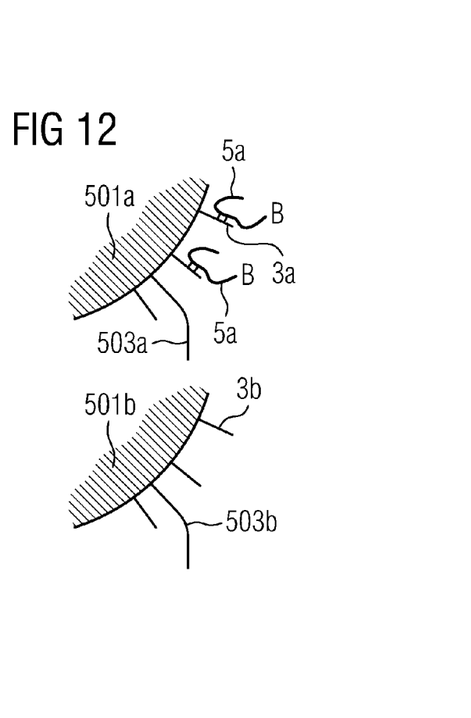

FIG. 12 depicts the situation after the magnetic beads 501a and 501b have been incubated with the solution containing the present DNA molecules 5a. Hybrids of the DNA molecules 5a and the oligonucleotide 3a have formed. Owing to the absence of the binding partner of corresponding oligonucleotides, no hybridization has occurred on the magnetic bead 501b.

The magnetic beads 501a and 501b are subsequently moved by a magnetic field to a surface of a biochip and held there. This is depicted in FIG. 13. The biochip 505 comprises two sensor fields, 507a and 507b. An oligonucleotide 509a which has a nucleic acid sequence which is partially complementary to the oligonucleotide 503a is immobilized on the sensor field 507a. Correspondingly, an oligonucleotide 509b which has a nucleic acid sequence which is partially complementary to the oligonucleotide 503b is immobilized on the sensor field 507b. In a manner similar to the process described above, concentrating the magnetic beads 501a and 501b and therefore the oligonucleotides 503a and 503b supports hybridization of the oligonucleotides 503a and 503b with the oligonucleotides 509a and 509b on the sensor fields 507a and 507b. After a sufficient incubation period, the magnetic field is switched off in order to remove non-immobilized magnetic beads 501a and 501b from the surface. As a result, the labeled DNA molecules 5a are bound merely by immobilization by way of the hybrid of oligonucleotides 503a and 509a above the sensor field 507a. Immobilization merely by the magnetic field above the sensor 507b is therefore ruled out. The DNA molecule 5a can then be detected by way of a label 511 at the site of the sensor field 507a by known detection processes. Assignment of the DNA molecule 5a to the sensor field 507a is unambiguous by way of specific binding of the DNA molecule 5a to the oligonucleotide 3a on the magnetic bead 501a and hybridization thereof via the oligonucleotide 503a with the oligonucleotide 509a at the sensor field 507a. This requires the removal of non-immobilized specimen of the magnetic beads 501a and 501b at the sensor surfaces. Because the supplied sample did not contain a binding partner for the oligonucleotide 3b, a DNA molecule will not be detected at the sensor field 507b, and the assay is therefore correspondingly negative.

In a manner similar to the abovementioned exemplary embodiment, this process can also be repeated cyclically, thereby enabling more species of the magnetic bead 501a to get close to the sensor surface 507a and immobilize there. This contributes to increasing the efficiency of concentration, in particular if few copies of the DNA molecule 5a are present.

The process described can be used universally because immobilization of the magnetic beads 501a and 501b is unspecific with regard to the DNA molecule to be detected, 5a. Detection specificity is achieved merely by forming the magnetic beads 501a and 501b and the oligonucleotides 3a and 3b immobilized thereon. The corresponding biochip 505 with the different sensor fields 507a and 507b is therefore suitable for detecting any kind of DNA molecules. Detection merely requires differently designed magnetic beads which can bind the DNA molecule to be detected.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004). The exemplary embodiments described have been limited by way of example to detection of a DNA molecule. They can, however, be used in a similar manner for any nucleic acid molecules or other biomolecules which can be bound specifically. Thus it is likewise possible to immobilize antibodies which are directed to proteins present in the sample for detection on the magnetic beads of the described processes. The magnetic beads can correspondingly be immobilized here optionally via the proteins themselves (exemplary embodiment 1) or via another protein with antibody or even a nucleic acid (exemplary embodiment 2).

The invention claimed is:

1. A process for concentrating nucleic acid molecules on a surface of a sensor field of a biochip of a sample, for detection of the nucleic acid molecules, comprising the following steps:
   (a) providing magnetic beads with transfer molecules immobilized thereon, which are configured to hybridize to a first portion of the nucleic acid molecules thereby forming complexes that comprise the magnetic beads, the transfer molecules, and the nucleic acid molecules;
   providing the surface of the sensor field, which forms a part of a surface of the biochip, wherein:
   capture molecules are immobilized on the surface of the sensor field;
   the capture molecules are configured to hybridize to a second portion of the nucleic molecules;
   and nucleic acid sequences of the capture molecules and the transfer molecules are selected such that a melting temperature of hybrids between the nucleic acid molecules and the transfer molecules is lower than a melting temperature of hybrids between the nucleic acid molecules and the capture molecules; and providing a magnetic field generator;
   (b) incubating the magnetic beads with the nucleic acid molecules at an incubating temperature of temperature $T_1$, which is below the melting temperature of the hybrids between the nucleic acid molecules and the transfer molecules such that the first portion of the nucleic acid molecules hybridize to the transfer molecule;
   (c) applying a magnetic field through the magnetic field generator such that the nucleic acid molecules bound to the magnetic beads are moved through the magnetic field to the surface of the sensor field;
   (d) increasing the incubating temperature from the temperature $T_1$ to a temperature $T_2$ which is above the melting temperature of the hybrids between the nucleic acid molecules and the transfer molecules, and which is below the melting temperature of the hybrids between the nucleic acid molecules and the capture molecules such that the nucleic acid molecules are detached from the magnetic beads and the second portion of the nucleic molecules are allowed to bind to the capture molecules;
   (e) moving the magnetic beads away from the surface of the biochip by switching off deactivating the magnetic field; and
   (f) repeating steps (b) to (e).

2. The process as claimed in claim 1, wherein the transfer molecules and the capture molecules are nucleic acids.

3. The process as claimed in claim 1, wherein
   first and second transfer molecules are provided on the magnetic beads,
   first and second capture molecules are provided on the surface of the sensor field,
   the first transfer molecules and the first capture molecules are particular to a first nucleic acid sequence, and
   the second transfer molecules and the second capture molecules are particular to a second nucleic acid sequence.

4. The process as claimed in claim 3, wherein
   the biochip has first and second separate sites,
   the first capture molecules are provided at the first separate site of the biochip, and the second capture molecules are provided at the second separate site of the biochip.

5. The process as claimed in claim 1, wherein different species of the magnetic beads are provided such that each species of the magnetic beads has one specific transfer molecule immobilized thereon that is capable of binding to a specific nucleic acid molecule to be detected.

* * * * *